United States Patent
Takahashi

(10) Patent No.: US 7,460,182 B2
(45) Date of Patent: Dec. 2, 2008

(54) CIRCUIT FOR PROCESSING VIDEO SIGNAL INCLUDING INFORMATION SUCH AS CAPTION

(75) Inventor: Tetsu Takahashi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 453 days.

(21) Appl. No.: 11/136,704

(22) Filed: May 25, 2005

(65) Prior Publication Data

US 2005/0231646 A1   Oct. 20, 2005

Related U.S. Application Data

(63) Continuation of application No. PCT/JP03/08210, filed on Jun. 27, 2003.

(51) Int. Cl.
*H04N 9/64* (2006.01)
*H04N 7/00* (2006.01)

(52) U.S. Cl. .................. 348/714; 348/468; 348/473; 348/478; 348/715

(58) Field of Classification Search .......... 348/714, 348/461, 468, 441, 458, 459, 448, 473, 476–479, 348/715
See application file for complete search history.

(56) References Cited

U.S. PATENT DOCUMENTS

| 5,699,124 A * | 12/1997 | Nuber et al. ............. 348/465 |
| 5,751,371 A | 5/1998 | Shintani |
| 6,111,589 A | 8/2000 | De Haan et al. |
| 6,263,396 B1 * | 7/2001 | Cottle et al. ............. 710/263 |
| 6,335,763 B1 * | 1/2002 | Nishio et al. ............. 348/564 |
| 6,553,566 B1 | 4/2003 | Grant et al. |
| 2004/0202455 A1 * | 10/2004 | Yanagihara et al. ......... 386/95 |

FOREIGN PATENT DOCUMENTS

| EP | 0 403 003 A1 | 12/1990 |
| JP | 8-181929 | 7/1996 |
| JP | 09-046630 | 2/1997 |
| JP | 10-322669 | 12/1998 |
| JP | 11-075113 | 3/1999 |
| JP | 2000-23119 | 1/2000 |
| JP | 2001-024983 A1 | 1/2001 |
| JP | 2001-069439 A1 | 3/2001 |
| JP | 2001-148835 | 5/2001 |
| JP | 2002-34040 | 1/2002 |
| JP | 2002-290894 | 10/2002 |
| WO | 95/06391 | 3/1995 |

* cited by examiner

*Primary Examiner*—M. Lee
(74) *Attorney, Agent, or Firm*—Arent Fox LLP

(57) ABSTRACT

A video signal processing circuit includes a frame memory to receive and store therein at a first rate each frame of a digital video signal in which additional information is assigned separately to each frame, a frame synchronization unit to read each frame of the digital video signal from the frame memory at a second rate, and a processing unit to assign the additional information to the digital video signal read by the frame synchronization unit, without repeating the additional information when the frame synchronization unit reads a same frame of the digital video signal repeatedly, and without skipping the additional information when the frame synchronization unit reads by skipping a frame of the digital video signal.

10 Claims, 5 Drawing Sheets

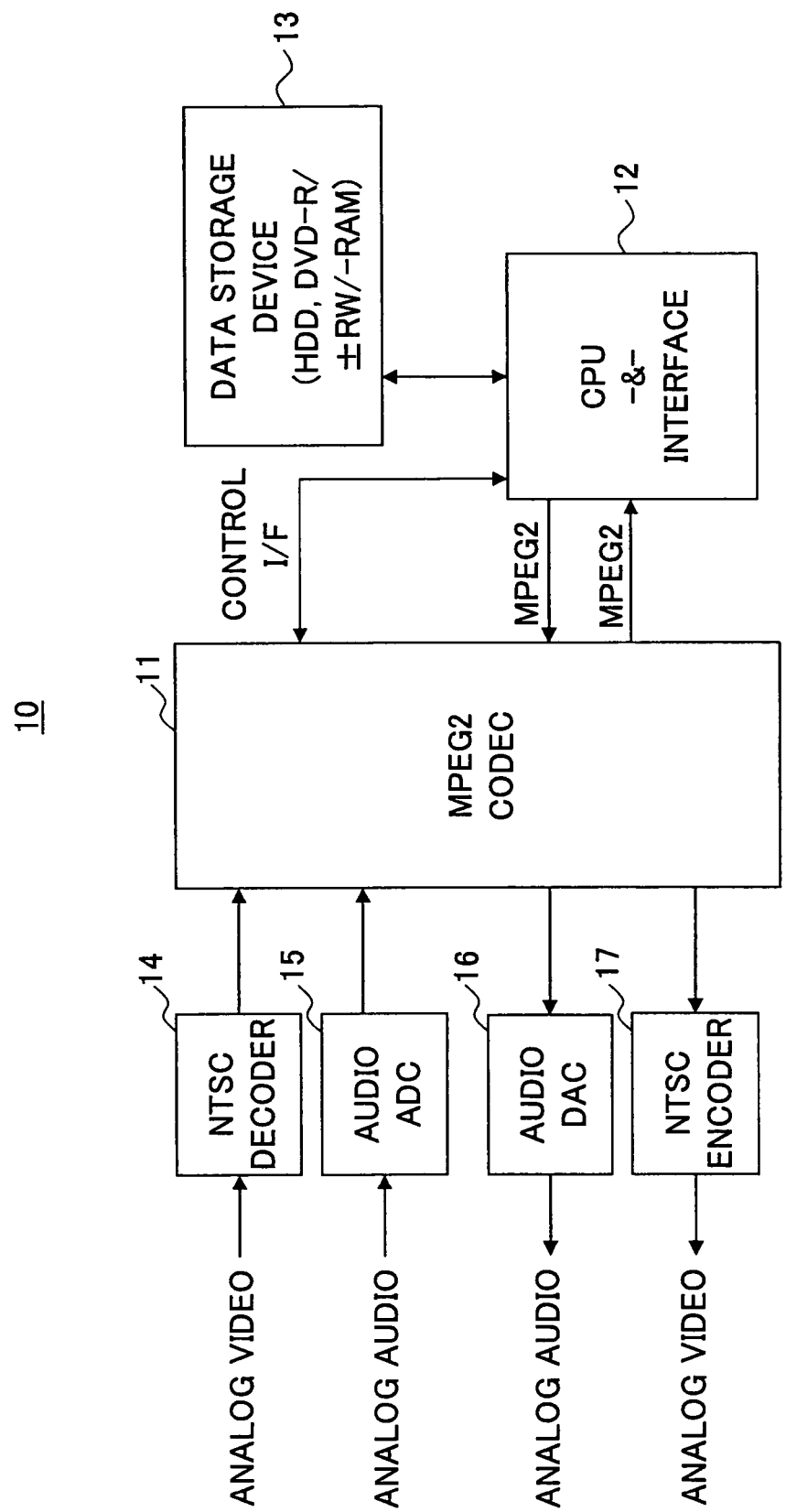

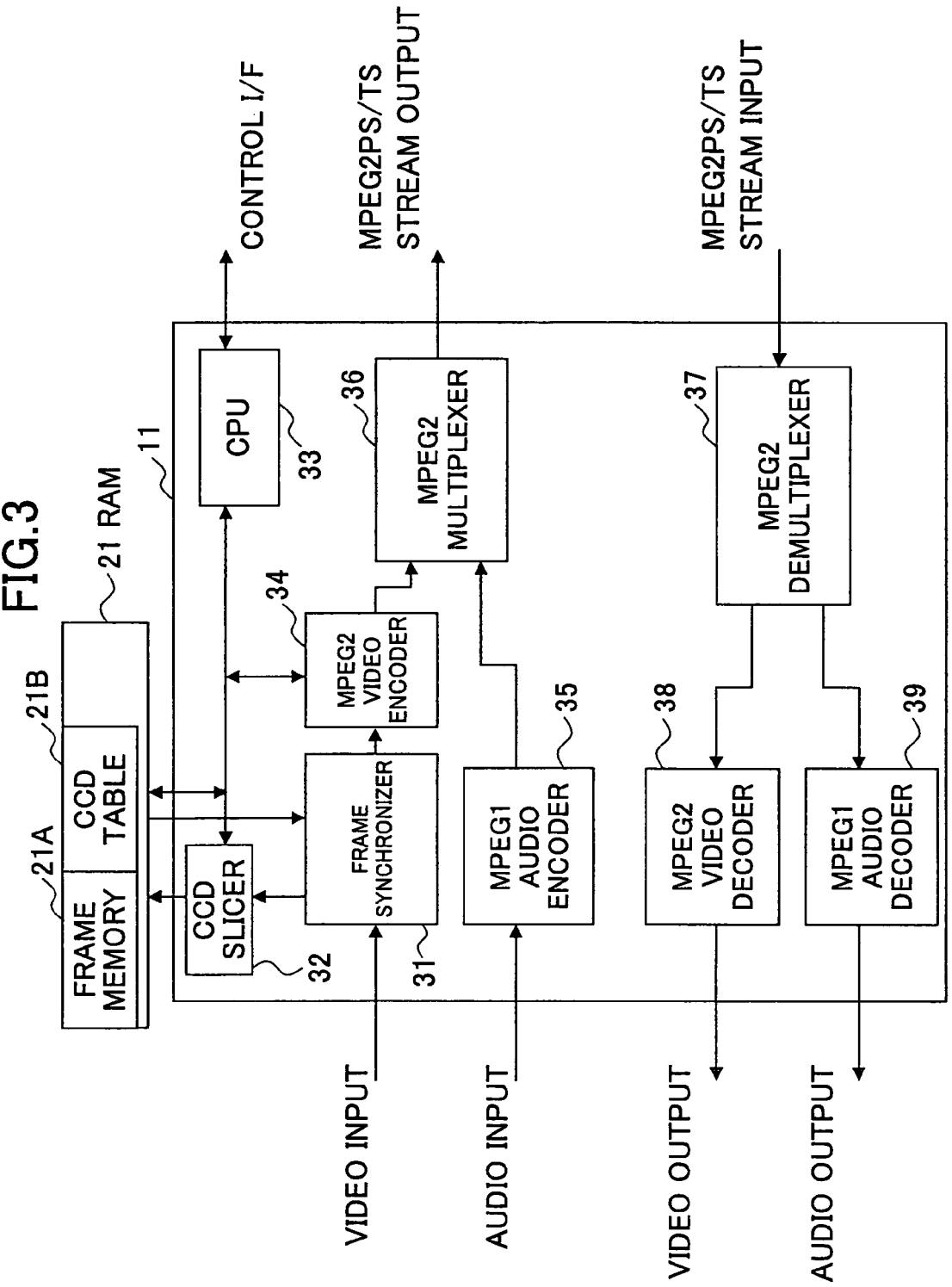

FIG.5A

| CCD | A | B | C | D | E | F | G | H |
|---|---|---|---|---|---|---|---|---|
| IMAGE | 1 | | 2 | | 3 | | 4 | |

FIG.5B

| CCD | A | B | C | D | E | F | G | H | I | J |
|---|---|---|---|---|---|---|---|---|---|---|
| IMAGE | 1 | | 3 | | 4 | | 5 | | | |

FIG.5C

| CCD | A | B | C | D | E | F | G | H |
|---|---|---|---|---|---|---|---|---|
| IMAGE | 1 | | 3 | | 4 | | 5 | |

FIG.5D

| CCD | A | B | C | D | E | F |
|---|---|---|---|---|---|---|
| IMAGE | 1 | | 2 | | 3 | |

FIG.5E

| CCD | A | B | C | D | E | F | G | H |
|---|---|---|---|---|---|---|---|---|
| IMAGE | 1 | | 2 | | 2 | | 3 | |

CIRCUIT FOR PROCESSING VIDEO SIGNAL INCLUDING INFORMATION SUCH AS CAPTION

CROSS-REFERENCE TO RELATED APPLICATION

This is a continuation of International Application No. PCT/JP2003/008210, filed on Jun. 27, 2003, the entire contents of which are hereby incorporated by reference.

BACKGROUND OF THE INVENTION

1. Field of the Invention

The present invention generally relates to video signal processing circuits, and particularly relates to a video signal processing circuit which performs encoding or the like of a video signal into which data such as caption information is inserted.

2. Description of the Related Art

Television signals these days include caption information such as closed captions, text broadcasting information, program listing information, copy guard signals, etc. Such information and signals are inserted into a plurality of horizontal lines located at the top of image fields, which include top fields and bottom fields in the case of video signals used in the interlace system, for example.

FIGS. 1A and 1B are drawings showing each field of the interlace system of the NTSC system and the position where text information or the like is inserted.

FIG. 1A shows a top field, and FIG. 1B shows a bottom field. As shown in FIG. 1A, the top field is comprised of horizontal scan lines from Line 1 to Line 263. Among the 263 horizontal scan lines, a portion from Line 1 to Line 21 at the top of the field is a blanking interval, which corresponds to a vertical blanking interval, and is not displayed on the screen. A vertical synchronizing pulse is inserted into this interval. The blanking interval may also include test signals, caption information, text broadcasting information, program listing information, copy guard signals, etc., inserted thereinto. By the same token, the bottom field shown in FIG. 1B is comprised of horizontal scan lines from Line 264 to Line 525. Among these, a portion from Line 264 to Line 284 at the top of the field is a blanking interval, into which caption information or the like may be inserted.

Text data used in the closed caption system is inserted, as 16-bit data for each field, into Line 21 of the top filed and Line 284 of the bottom field. Among the 16 bits, 2 bits are used as parity bits. Text data that may be one character for each frame may be extracted and put together to form a caption comprised of a plurality of characters, which is then superimposed on video information for the period specified by control information, thereby producing a movie subtitle or the like.

Video-and-audio signals supplied as analog signals through television broadcast, for example, may be recorded as digital signals. In such a case, the video-and-audio signals are converted into digital signals by a NTSC decoder and audio DAC (digital-to-analog converter). The converted digital signals are supplied to an MPEG2 codec for coding so as to be compressed into an MPEG2PS-system or MPEG2TS-system stream. The compressed stream is output from a port dedicated for stream of the MPEG2 codec, and is transferred by a CPU through DMA to a recording device for storage therein.

In so doing, the MPEG2 codec extracts text data inserted into Line 21 and Line 284 of the video frame coded by the MPEG2 codec, and inserts the extracted text data into the stream.

In general, the clock frequency of digital data output from an NTSC decoder (i.e., the speed at which the analog signals are supplied) is slightly different from the clock frequency with which the MPEG2 codec operates (i.e., the speed at which coding is performed). In order to absorb such a difference between the speed of data supply and the speed of coding, provision is made such that the digital data of each frame output from the NTSC decoder is temporarily stored in a buffer, and the frame data are then successively read from the buffer for coding. With the provision of the buffer, the MPEG2 codec may skip a frame or repeat a frame as such need arises at the time of coding so as to absorb the difference between the speed of data supply and the speed of coding.

In this manner, the speed difference is absorbed. Since text data or the like are inserted into each field of a video signal sequentially, however, the skipping or repeating of a frame results in the data being lost, or the same data being repeated twice. That is, if repeating is done, a caption intended to be "TEST" may become "TEEST" because of repetition of the same data occurring twice. If skipping is done, a caption intended to be "TEST" may become "TET" because of the loss of certain data.

In consideration of this, it is desirable to absorb a difference between the speed of signal supply and the speed of signal processing without undermining consistency of text information or the like at the time of processing a video signal in which the text information or the like is inserted into each frame or into each field.

[Patent Document 1] Japanese Patent Application PCT-based Publication No. 9-501808

[Patent Document 2] Japanese Patent Application Publication No. 2001-24983

[Patent Document 3] Japanese Patent Application Publication No. 2001-69439

[Patent Document 2] Japanese Patent Application Publication No. 11-75113

SUMMARY OF THE INVENTION

It is a general object of the present invention to provide a video signal processing circuit that substantially obviates one or more problems of the related art described above.

It is another and more specific object of the present invention to provide a video signal processing circuit that can absorb a difference between the speed of signal supply and the speed of signal processing without undermining consistency of text information or the like at the time of processing a video signal in which the text information or the like is inserted into each frame or into each field.

In order to achieve the above objects, a video signal processing circuit according to the present invention includes a frame memory to receive and store therein at a first rate each frame of a digital video signal in which additional information is assigned separately to each frame, a frame synchronization unit to read each frame of the digital video signal from the frame memory at a second rate, and a processing unit to assign the additional information to the digital video signal read by the frame synchronization unit, without repeating the additional information when the frame synchronization unit reads a same frame of the digital video signal repeatedly, and without skipping the additional information when the frame synchronization unit reads by skipping a frame of the digital video signal.

According to the video signal processing circuit described above, even when a frame is repeatedly read or skipped due to a difference between the first rate and the second rate, the additional information such as text information or the like is processed such as to be assigned to a video stream without repeating or skipping thereof. This makes it possible to absorb a difference between the speed of signal supply and the speed of signal processing without undermining consistency of text information or the like at the time of processing a video signal in which the text information or the like is inserted into each frame or into each field.

BRIEF DESCRIPTION OF THE DRAWINGS

Other objects and further features of the present invention will be apparent from the following detailed description when read in conjunction with the accompanying drawings, in which:

FIG. 2 is a drawing showing an example of a video signal processing circuit to which the present invention is applied;

FIG. 3 is a block diagram showing the configuration of the MPEG2 codec and a memory coupled thereto;

FIGS. 5A through 5E are drawings showing comparison between the present invention and the related art with respect to correspondences between the frames and closed caption data of video data.

DESCRIPTION OF THE PREFERRED EMBODIMENTS

Figure 1A:
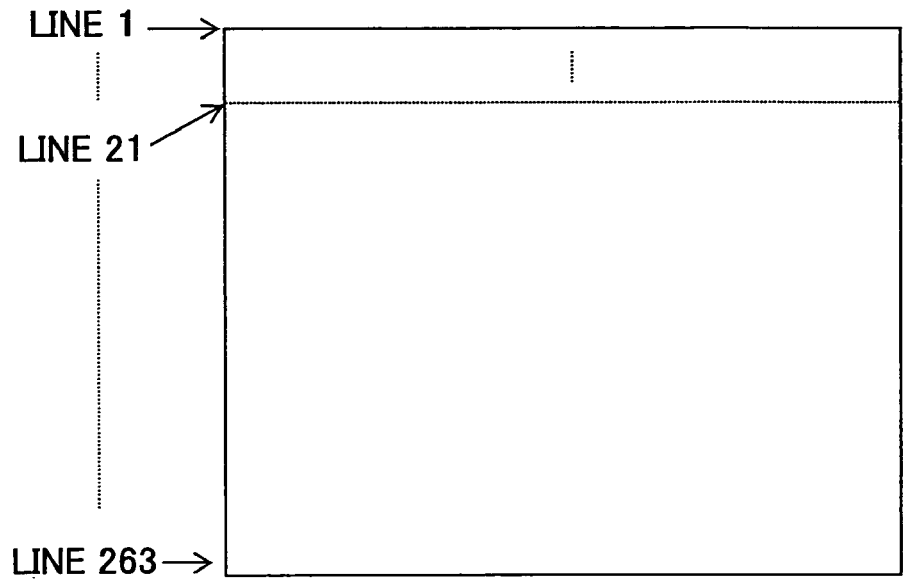
FIGS. 1A and 1B are drawings showing each field of the interlace system and the position where text information or the like is inserted.
Figure 1B:
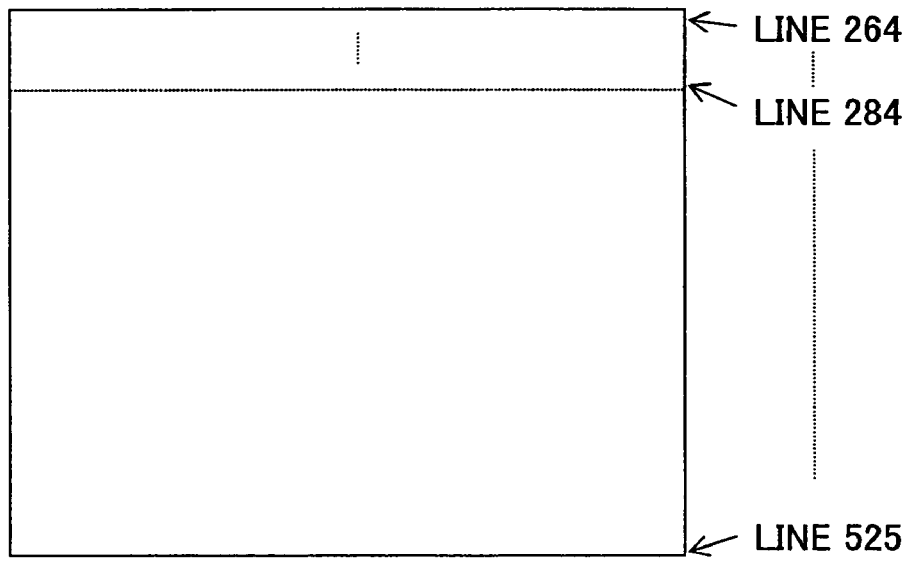

In the following, embodiments of the present invention will be described with reference to the accompanying drawings.

FIG. 2 is a drawing showing an example of a video signal processing circuit to which the present invention is applied.

A video signal processing circuit 10 of FIG. 2 includes an MPEG2 codec 11, a CPU-&-interface 12, a data storage device 13, an NTSC decoder 14, an audio ADC 15, an audio DAC 16, and an NTSC encoder 17. Here, ADC stands for analog-to-digital converter, and DAC stands for digital-to-analog converter.

An analog video signal and analog audio signal supplied through television broadcasting, for example, may be input into the NTSC decoder 14 and the audio ADC 15, respectively. The NTSC decoder 14 converts the analog video signal into a digital video signal for provision to the MPEG2 codec 11. The audio ADC 15 coverts the analog audio signal into a digital audio signal for provision to the MPEG2 codec 11.

The MPEG2 codec 11 temporarily stores the digital video signal in a frame memory according to the frame rate at which the data is supplied. Further, the MPEG2 codec 11 reads data for one frame from the frame memory according to the frame rate that the MPEG2 codec 11 requires. With this operation, the same frame is repeatedly read if the required frame rate is faster than the supply frame rate, and a frame is skipped halfway through if the required frame rate is slower than the supply frame rate.

The MPEG2 codec 11 encodes the video data read from the frame memory, and multiplexing the encoded video data with the audio data that is encoded on a separate path, followed by supplying the multiplexed data to the CPU-&-interface 12 as a compressed MPEG2 stream. The CPU-&-interface 12 transfers the supplied stream to the data storage device 13.

The data storage device 13 is a hard disk drive, a DVD drive, or the like, for example, and stores the stream comprised of the video data and audio data in a record medium.

At the time of decoding such as reproduction, the CPU-&-interface 12 reads a stream comprised of video data and audio data from the data storage device 13, and demultiplexes the stream into the video data and the audio data, followed by decoding the respective data. The decoded audio data is converted by the audio DAC 16 into an analog audio signal. The decoded video data is converted by the NTSC encoder 17 into an analog video signal.

FIG. 3 is a block diagram showing the configuration of the MPEG2 codec 11 and a memory coupled thereto.

The MPEG2 codec 11 shown in FIG. 3 is coupled to a RAM 21. The RAM 21 includes a frame memory 21A for storing a video signal on a frame-by-frame basis and a CCD table 21B for storing closed caption data (CCD).

The MPEG2 codec 11 of FIG. 3 includes a frame synchronizer 31, a CCD slicer 32, a CPU 33, an MPEG2 video encoder 34, an MPEG1 audio encoder 35, an MPEG2 multiplexer 36, an MPEG2 demultiplexer 37, an MPEG2 video decoder 38, and an MPEG1 audio decoder 39.

The frame synchronizer 31 writes a supplied digital video signal to the frame memory 21A of the RAM 21 via the CCD slicer 32. The frame memory 21A has a two-bank configuration in which each bank has a memory capacity for one frame to store video data for one frame. The frame synchronizer 31 writes the supplied video signal to the two banks of the frame memory 21A alternately. When the writing of video data for one frame to one bank comes to an end, an interruption (frame interruption) is issued to the CPU 33.

In response to a request from the MPEG2 video encoder 34, the frame synchronizer 31 reads video data for one frame from the frame memory 21A, and transfers the retrieved video data to the MPEG2 video encoder 34. In so doing, the bank serving as the transfer source from which the video data for one frame is read is the bank which stores therein chronologically old video data. Accordingly, among the two frames stored in the frame memory 21A, the one stored before the other is always transferred before the other.

The video signal supplied from an exterior is not in synchronization with the requests of the MPEG2 video encoder 34. Accordingly, there may be a slight difference between the frame rate of the video signal supplied from the exterior and the frame rate at which the MPEG2 video encoder 34 issues the requests. Even in such a case, the difference in the frame rate is absorbed as the frame synchronizer 31 responding to a request from the MPEG2 video encoder 34 always reads an older one among the two frame data in the manner as described above. Namely, if the rate of requests from the MPEG2 video encoder 34 is higher, a process of skipping a frame (skipping process) is performed. If the rate of request from the MPEG2 video encoder 34 is lower, a process of transferring the same frame (repeating process) is performed.

The frame synchronizer 31 detects the execution of a skipping process or repeating process, and stores data indicative of which process is performed in a register provided in the frame synchronizer at the time of start of frame transfer. When transferring a frame to the MPEG2 video encoder 34, further, the frame synchronizer 31 interrupts the CPU 33 (encode start interruption) at the time of start of transfer of the data provided at the beginning of the frame (after the setting of the register if the skipping or repeating is done). The CPU 33 responds to this interruption to read from the above-noted register the data indicative of either a skipping process or a repeating process, thereby learning which process has been performed.

The CCD slicer 32 extracts 16-bit CCD (closed caption data) from each field of the supplied video signal, and stores the extracted CCD in an internal register. Further, a register for indicating whether CCD is detected is also provided. The CPU 33 responds to the frame interruption to read those registers, thereby extracting the presence/absence of CCD and CCDs of both fields, which are then stored in work memory of the CPU 33. In response to the skipping/repeating process of a frame, the CPU 33 applies a predetermined process to the CCD, and writes the CCD data to the CCD table 21B set aside in a predetermined space of the RAM 21. The timing at which this writing is performed is responsive to the encode start interruption.

The MPEG2 video encoder 34 successively encodes the video data of individual frames transferred from the frame memory 21A by the frame synchronizer 31, thereby generating an MPEG2 video stream. Further, the MPEG2 video encoder 34 inserts the CCD stored in the CCD table 21B successively into the MPEG2 video stream.

The MPEG1 audio encoder 35 encodes audio data supplied from an exterior for provision to the MPEG2 multiplexer 36. The MPEG2 multiplexer 36 multiplexes the MPEG2 video stream supplied from the MPEG2 video encoder 34 and the MPEG1 audio stream supplied from the MPEG1 audio encoder 35 for provision to an exterior as an MPEG2PS/TS stream.

The MPEG2 demultiplexer 37 demultiplexes an MPEG2PS/TS stream supplied from an exterior into a video stream and an audio stream for provision to the MPEG2 video decoder 38 and the MPEG1 audio decoder 39, respectively. The MPEG2 video decoder 38 decodes the video stream for provision as a video output to an exterior. The MPEG1 audio decoder 39 decodes the audio stream for provision as an audio output to an exterior.

Figure 4:
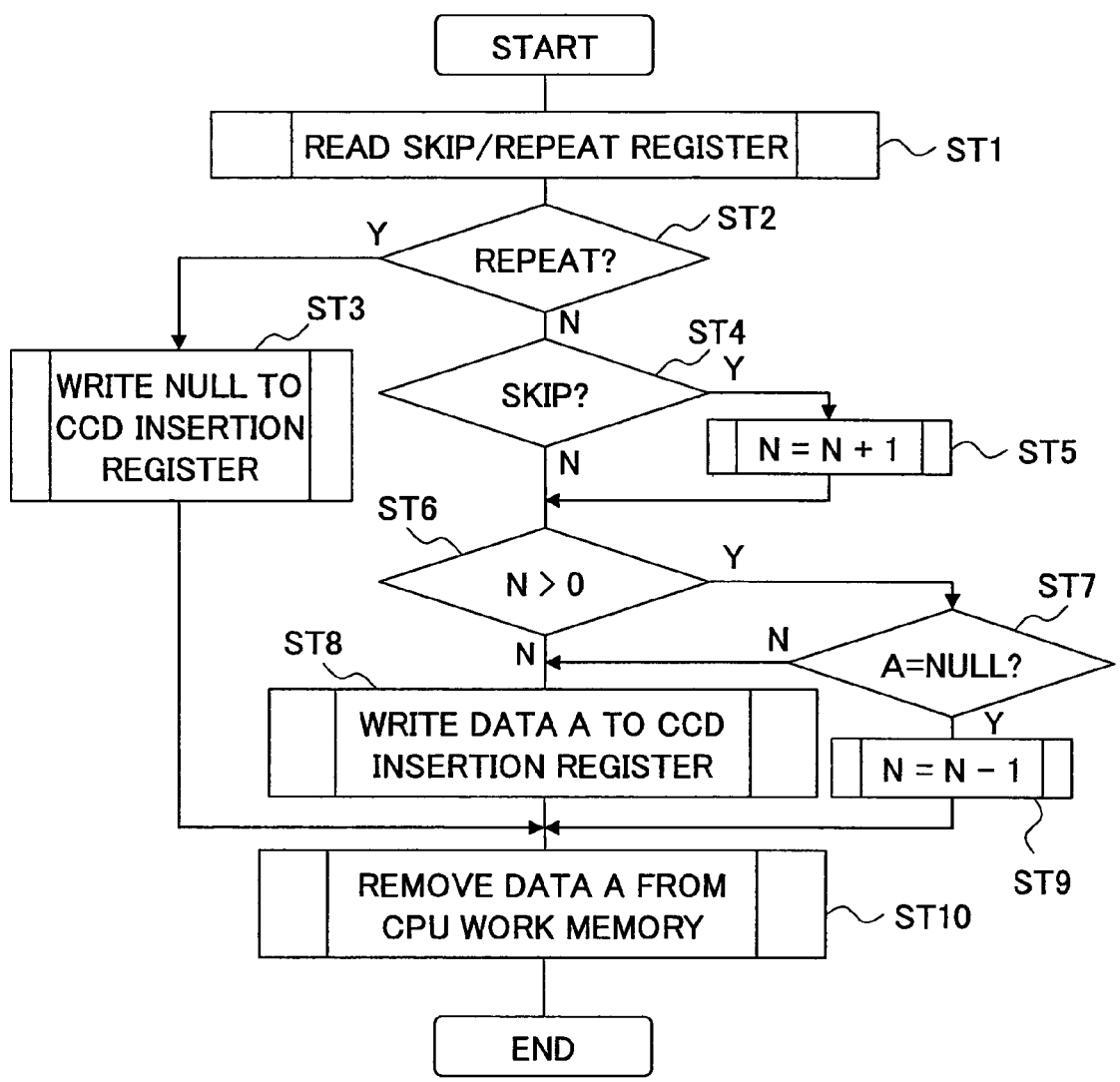
FIG. 4 is a flowchart showing a process applied to CCD by the CPU in response to the skipping/repeating of a frame.

FIG. 4 is a flowchart showing a process applied to CCD by the CPU 33 in response to the skipping/repeating of a frame. As previously described, this process is performed at the time the CPU 33 writes CCD data to the CCD table 21B.

First, a description will be given of a process that is performed when neither a skipping process nor a repeating process is performed (frames are transferred in a routine manner).

At step ST1 of FIG. 4, the CPU 33 reads data indicative of either a skipping process or a repeating process from the internal register (skip/repeat register) of the frame synchronizer 31.

At step ST2, the CPU 33 checks whether the content of the skip/repeat register indicates a repeating process. Since a normal case without repeating is observed, the procedure goes to step ST4.

At step ST4, the CPU 33 checks whether the content of the skip/repeat register indicates a skipping process. Since a normal case without skipping is observed, the procedure goes to step ST6.

At step ST6, the CPU 33 checks whether N is more than 0. Here, N is a count that initially starts at 0, and is incremented by one each time a skipping process is performed (step ST5). The case in which N is more than 0 will be described later. Here, N is assumed to be 0.

At step ST8, the CPU 33 writes data A to the CCD table 21B (CCD insertion register). Here, the data A is the oldest CCD stored in the CPU work memory area.

At step ST10, the data A is removed from the work memory area of the CPU 33.

In the manner described above, CCD is transferred from the work memory area of the CPU 33 to the CCD table 21B in the same order as the frame sequence when the frames are transferred in a routine manner.

Next, a description will be given of a process that is performed when a repeating process is performed.

At step ST1 of FIG. 4, the CPU 33 reads data indicative of either a skipping process or a repeating process from the internal register (skip/repeat register) of the frame synchronizer 31.

At step ST2, the CPU 33 checks whether the content of the skip/repeat register indicates a repeating process. Since an indication of repeating is observed, the procedure goes to step ST3.

At step ST3, the CPU 33 writes NULL (code indicating the absence of data) to the CCD table 21B (CCD insertion register).

At step ST10, thereafter, the data A is removed from the work memory area of the CPU 33.

In the manner described above, NULL is written without repeating a CCD corresponding to a repeated frame when the frame is repeated. Provision is thus made to avoid the repeated displaying of character data corresponding to the repeated frame.

Here, the operation of writing NULL in response to a repeating process is necessary in order to maintain correct timing relationship between frames and character data. If NULL is not written in response to a repeating process, character data corresponding to the next frame is assigned to the frame that is repeated by the repeating process. The writing of NULL in response to a repeating process as described above ensures that correspondences between frames and character data are properly maintained.

The operation of writing NULL in response to a repeating process does not have to be performed at the time of the frame that is repeated. Nothing may be written when the repeating process is performed, and the fact that the repeating process is performed may be recorded. At any one of the subsequent frames, then, NULL may be written by finding a proper occasion. With such provision, it is also possible to return the correspondences between frames and character data to a correct timing relationship after they are misaligned by the repeating process. Alternatively, an extra NULL may be written in advance, and nothing may be written when a repeating process is performed. That is, the timing is set to deviate in advance, and is returned to correct timing at the time a repeating process is performed. Regardless of which measure is taken, what is important is to insert NULLs equal in number to the performed repeating processes at proper timing, thereby keeping correct correspondences between the frames and the character data in the long run.

In the following, a description will be given of a case in which a skipping process is performed.

At step ST1 of FIG. 4, the CPU 33 reads data indicative of either a skipping process or repeating process from the internal register (skip/repeat register) of the frame synchronizer 31.

At step ST2, the CPU 33 checks whether the content of the skip/repeat register indicates a repeating process. Since the case of a skipping process rather than a repeating process is observed, the procedure goes to step ST4.

At step ST4, the CPU 33 checks whether the content of the skip/repeat register indicates a skipping process. Since the case of a skipping process is observed, the procedure goes to step ST5.

At step ST5, the count N is incremented by one. As previously described, N is a count that initially starts at 0, and is incremented by one each time a skipping process is performed.

At step ST6, the CPU 33 checks whether N is more than 0. In this case, N is more than 0, so that the procedure proceeds to step ST7.

At step ST7, the CPU 33 checks whether the data A that is the oldest CCD in the CPU work memory area is NULL or not. In the case of subtitle data, for example, the data rate of CCD is much higher than the data rate of characters corresponding to ordinary conversations, so that it is reasonable to believe that CCD associated with a given frame may often be comprised of NULL data. If it is not NULL data, the procedure proceeds to step ST8.

At step ST8, the CPU 33 writes the data A to the CCD table 21B (CCD insertion register).

At step ST10, the data A is removed from the work memory area of the CPU 33.

If it is found at step ST7 that the data A, i.e., the oldest CCD in the CPU work memory area, is NULL, N is decremented by one at step ST9. The data A is then removed at step ST10 without writing the data A (NULL) to the CCD table 21B. Accordingly, even when a frame is skipped, the CCD is discarded if this corresponding CCD is unnecessary data (NULL) This can maintain correct timing relationships between frames and CCD.

If a frame is skipped and the corresponding CCD is necessary data (i.e., N at step ST7), CCD is written at step ST8. This results in the timing relationship between the frames and the CCD being misaligned. In this case, step ST9 is not carried out, so that N stays at a value larger than 0. When there is thereafter an occasion on which neither skipping nor repeating is performed (i.e., a frame is transferred in a routine manner), N is found to be more than 0 at step ST6, resulting in step ST7 being performed. If it is found at step ST7 that the data A that is the oldest CCD in the CPU work memory area is NULL, this CCD is discarded, thereby restoring the timing between the frames and the CCD to a correct relationship. If a plurality of skipping processes are performed to result in a large N, a single disposal of CCD does not restore the timing to a correct relationship, and a plurality of disposals are necessary before the timing returns to a correct relationship.

In the manner described above, necessary CCD is transferred from the CCD work memory area to the CCD table 21B even in the case of execution of a skipping process, which prevents caption characters from being skipped. Further, NULL data is skipped as appropriate by taking into account the timing between frames and CCD, thereby maintaining or restoring a correct timing relationship between the frames and the CCD.

FIGS. 5A through 5E are drawings showing comparison between the present invention and the related art.

FIG. 5A is a drawing showing relationship between "IMAGE" that is frames of video data supplied as inputs from an exterior and the "CCD" that is closed caption data. As illustrated, CCD(A, B) is inserted into IMAGE1, CCD(C, D) into IMAGE2, CCD(E, F) into IMAGE3, and CCD(G, H) into IMAGE4.

FIG. 5B is a drawing showing a video stream that is obtained conventionally in the case where FRAME2 is skipped. As illustrated, IMAGE2 is skipped, together with which CCD(C, D) is also skipped, resulting in the caption intended as "ABCDEFGH" ending up being "ABEFGH".

FIG. 5C is a drawing showing a video stream that is obtained by the present invention in the case where FRAME2 is skipped. As illustrated, IMAGE2 is skipped, but corresponding CCD(C, D) is retained without being discarded, resulting in the caption intended as "ABCDEFGH" being properly displayed.

FIG. 5D is a drawing showing a video stream that is obtained conventionally in the case where FRAME2 is repeated. As illustrated, IMAGE2 is repeated, together with which CCD(C, D) is also repeated. As a result, the caption intended as "ABCDEFGH" ends up being "ABCDCDEFGH".

FIG. 5E is a drawing showing a video stream that is obtained by the present invention in the case where FRAME2 is repeated. As illustrated, IMAGE2 is repeated, but corresponding CCD(C, D) is processed without repetition, resulting in the caption intended as "ABCDEFGH" being properly displayed.

Although the present invention has been described with reference to embodiments, the present invention is not limited to these embodiments. Various variations and modifications may be made without departing from the scope of the claimed invention.

For example, the disclosed embodiments are configured such that hardware detects skipping and repeating. Alternatively, software-based processing by the CPU may detect them by counting and comparing the numbers of frame interruptions and encode start interruptions.

Further, these embodiments have been described with reference to closed caption as an example. The present invention is not limited to such caption information, but is also applicable to information in general that is inserted into a blanking period or the like for each frame, such as test signals, text broadcasting information, program listing information, copy guard signals, etc.

Moreover, these embodiments are configured such that a check is made as to whether the attached data (CCD) of a skipped frame is NULL or not, followed by skipping the attached data also if the data is NULL. Alternatively, a check may be made as to whether the attached data of a skipped frame is important or not, followed by skipping the attached data also if the data is not important. A determination as to whether given data is important is dependent on the type of the attached information (i.e., types such as program listing information, copy guard signals, etc.). Accordingly, data that can be skipped (data of low importance) and data that cannot be skipped (data of high importance) may be determined in advance according to the type of the attached information.

What is claimed is:

1. A video signal processing circuit, comprising:
    a frame memory to receive and store therein at a first rate each frame of a digital video signal in which additional information is assigned separately to each frame;
    a frame synchronization unit to read each frame of the digital video signal from said frame memory at a second rate; and
    a processing unit to assign the additional information to the digital video signal read by said frame synchronization unit, without repeating the additional information when said frame synchronization unit reads a same frame of the digital video signal repeatedly, and without skipping the additional information when said frame synchronization unit reads by skipping a frame of the digital video signal.

2. The video signal processing circuit as claimed in claim 1, further comprising a video encoder to encode each frame of the digital video signal read from said frame memory by said frame synchronization unit.

3. The video signal processing circuit as claimed in claim 1, wherein said additional information is text information.

4. The video signal processing circuit as claimed in claim 3, wherein when said frame synchronization unit reads a same frame of the digital video signal twice consecutively, said processing unit replaces the additional information corresponding to the frame read the second time with NULL data.

5. The video signal processing circuit as claimed in claim 1, wherein when said frame synchronization unit reads by skipping a frame of the digital video signal, said processing unit discards the additional information corresponding to the skipped frame if the corresponding additional information is data of predetermined low importance, and retains the corresponding additional information if the corresponding additional information is not the data of predetermined low importance.

6. The video signal processing circuit as claimed in claim 1, wherein when the additional information is not skipped despite a fact that a frame of the digital video signal is skipped, said processing unit skips the additional information corresponding to a subsequent frame in response to detection that the additional information corresponding to the subsequent frame is data of predetermined low importance.

7. The video signal processing circuit as claimed in claim 6, wherein the data of low importance is NULL data.

8. A video signal processing method, comprising the steps of:

detecting whether a frame of a digital video signal in which additional information is assigned separately to each frame is subjected to repeating or skipping; and processing the additional information in response to a result of the detecting, without skipping the additional information when said skipping due to skipping a frame of the digital video signal is detected.

9. The video signal processing method as claimed in claim 8, wherein said step of processing the additional information includes a step of, in response to detection of said repeating due to repeating a same frame of the digital video signal twice consecutively, replacing the additional information corresponding to the frame read the second time with NULL data.

10. The video signal processing method as claimed in claim 8, wherein said step of processing the additional information includes a step of, in response to detection of said skipping due to skipping a frame of the digital video signal, discarding the additional information corresponding to the skipped frame if the corresponding additional information is data of predetermined low importance, and retaining the corresponding additional information if the corresponding additional information is not the data of predetermined low importance.

* * * * *